United States Patent
Collier et al.

(10) Patent No.: US 9,828,314 B2
(45) Date of Patent: Nov. 28, 2017

(54) HYDROCHLORIC ACID PURIFICATION PROCESS

(71) Applicant: Arkema France, Colombes (FR)

(72) Inventors: Bertrand Collier, Saint-genis-laval (FR); Dominique Deur-Bert, Charly (FR); Joaquin Lacambra, Vernaison (FR); Anne Pigamo, Francheville (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/039,294

(22) PCT Filed: Nov. 10, 2014

(86) PCT No.: PCT/FR2014/052868
§ 371 (c)(1),
(2) Date: May 25, 2016

(87) PCT Pub. No.: WO2015/079137
PCT Pub. Date: Jun. 4, 2015

(65) Prior Publication Data
US 2017/0158586 A1  Jun. 8, 2017

(30) Foreign Application Priority Data
Nov. 28, 2013  (FR) ..................................... 13 61736

(51) Int. Cl.
*C07C 17/20* (2006.01)
*C07C 17/25* (2006.01)
(Continued)

(52) U.S. Cl.
CPC ............ *C07C 17/206* (2013.01); *B01D 53/04* (2013.01); *B01D 53/78* (2013.01); *B01D 53/869* (2013.01);
(Continued)

(58) Field of Classification Search
CPC .... B01D 53/04; B01D 53/78; B01D 53/8662; B01D 53/869; B01D 2251/50;
(Continued)

(56) References Cited

U.S. PATENT DOCUMENTS 3,074,779 A  1/1963  Paterson
3,353,911 A  11/1967  Leopold et al.
(Continued)

FOREIGN PATENT DOCUMENTS

EP  0939071 A1  9/1999
FR  1 507 252 A  12/1967
(Continued)

OTHER PUBLICATIONS

International Search Report dated Jan. 26, 2015 for PCT/FR2014/052868.

*Primary Examiner* — Medhanit Bahta
(74) *Attorney, Agent, or Firm* — Brinks Gilson & Lione

(57) ABSTRACT

The invention relates to a process for the treatment of a gas stream comprising hydrochloric acid, hydrofluoric acid and fluorinated/oxygenated compounds, in which the gas stream is successively subjected to:
- a stage of catalytic hydrolysis;
- a stage of washing with an acid solution;
- a stage of adsorption of impurities by active charcoal;
- a stage of adiabatic or isothermal absorption of the hydrochloric acid in an aqueous solution, making it possible to collect hydrochloric acid solution.

11 Claims, 1 Drawing Sheet

(51) Int. Cl.
*C01B 7/07* (2006.01)
*B01D 53/78* (2006.01)
*B01D 53/86* (2006.01)
*C07C 17/395* (2006.01)
*B01D 53/04* (2006.01)

(52) U.S. Cl.
CPC ........ *B01D 53/8662* (2013.01); *C01B 7/0706* (2013.01); *C01B 7/0718* (2013.01); *C01B 7/0725* (2013.01); *C07C 17/25* (2013.01); *C07C 17/395* (2013.01); *B01D 2251/50* (2013.01); *B01D 2251/502* (2013.01); *B01D 2253/102* (2013.01); *B01D 2253/106* (2013.01); *B01D 2257/2047* (2013.01); *B01D 2257/2066* (2013.01); *Y02C 20/30* (2013.01); *Y02P 20/154* (2015.11)

(58) Field of Classification Search
CPC ........ B01D 2251/502; B01D 2253/102; B01D 2253/106; B01D 2257/2047; B01D 2257/2066; C01B 7/0706; C01B 7/0725; C07C 17/206; Y02C 20/30; Y02P 20/154
See application file for complete search history.

(56) References Cited

U.S. PATENT DOCUMENTS

| | | |
|---|---|---|
| 3,464,787 A | 9/1969 | Carson |
| 3,617,209 A | 11/1971 | Massonne et al. |
| 4,902,838 A | 2/1990 | Manzer et al. |
| 6,790,421 B2* | 9/2004 | Mori ................. B01D 53/8659 422/177 |
| 7,976,808 B2* | 7/2011 | Sakurai ................ B01D 53/685 423/240 S |

FOREIGN PATENT DOCUMENTS

| | | |
|---|---|---|
| FR | 2 019 406 A1 | 7/1970 |
| GB | 1 156 560 | 7/1969 |
| WO | WO 02/099005 A1 | 12/2002 |
| WO | WO 2007/079431 A2 | 7/2007 |
| WO | WO 2008/040969 A2 | 4/2008 |
| WO | WO 2008/054781 A1 | 5/2008 |
| WO | WO 2009/118628 A1 | 10/2009 |

* cited by examiner

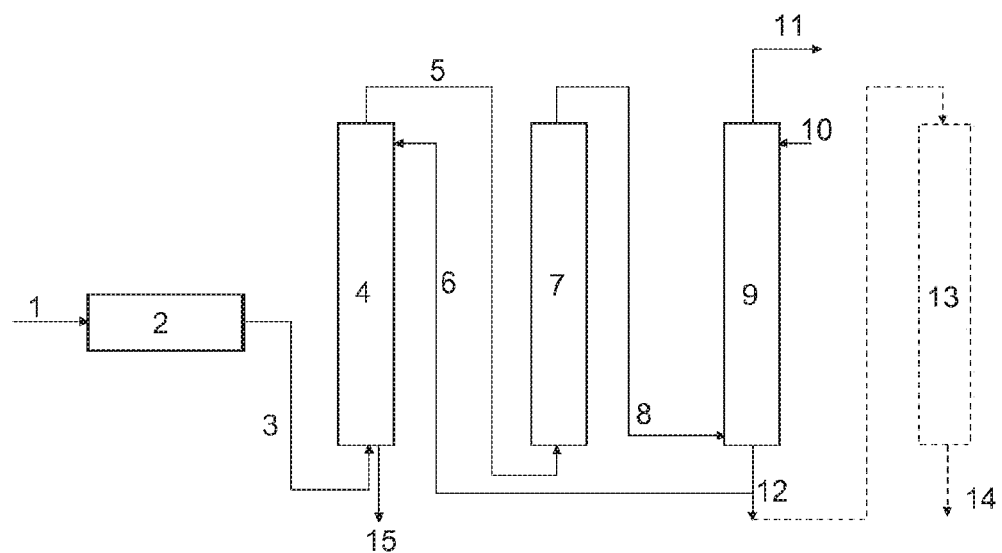

HYDROCHLORIC ACID PURIFICATION PROCESS

This application is a U.S. National Stage application of International Application No. PCT/FR2014/052868, filed Nov. 10, 2014, which claims the benefit of French Application No. 13.61736, filed Nov. 28, 2013.

FIELD OF THE INVENTION

The present invention relates to a process for the purification of hydrochloric acid and to a plant suitable for the implementation of this process. The invention can in particular be used in the context of the treatment of effluents resulting from a catalytic fluorination reaction.

TECHNICAL BACKGROUND

It is known to produce fluorinated compounds, such as hydrofluorocarbons, by fluorination of chlorinated compounds, such as hydrochlorocarbons in particular. This fluorination is generally a catalytic fluorination using hydrofluoric acid (HF) as fluorinating agent.

During this type of reaction, hydrochloric acid (HCl) is coproduced. It is known to separate the HCl from the other gases produced via a distillation column and then to absorb the HCl in an adiabatic absorption column in order to generate an HCl solution of commercial type.

The document FR 1507252 describes stages of treatment on active charcoal, at high temperature and in the presence of water, and of washing with concentrated aqueous hydrochloric acid.

The document U.S. Pat. No. 3,353,911 describes the purification of an HF/HCl gas mixture by bringing into contact with an absorbent solution which is a saturated boric acid solution.

However, the known techniques for the purification of hydrochloric acid do not make it possible, in some cases, to achieve the required HCl purity.

There thus exists a need to provide an improved process for the purification of hydrochloric acid in a gas stream.

SUMMARY OF THE INVENTION

The invention relates first to a process for the treatment of a gas stream comprising hydrochloric acid, hydrofluoric acid and fluorinated-oxygenated compounds, in which the gas stream is successively subjected to:
- a stage of catalytic hydrolysis;
- a stage of washing with an acid solution;
- a stage of adsorption of impurities by active charcoal;
- a stage of adiabatic or isothermal absorption of the hydrochloric acid in an aqueous solution, making it possible to collect hydrochloric acid solution.

According to one embodiment, the stage of catalytic hydrolysis is carried out on a bed of active charcoal.

According to one embodiment, the acid solution used during the washing stage is a hydrochloric acid solution and preferably originates from the hydrochloric acid solution collected on conclusion of the adiabatic or isothermal absorption stage.

According to one embodiment, the process additionally comprises:
- a stage of bringing the hydrochloric acid solution into contact with a silica gel.

According to one embodiment, the fluorinated-oxygenated compounds comprise carbonyl difluoride, carbonyl chloride fluoride, trifluoroacetyl fluoride and/or trifluoroacetic acid and, preferably, the gas stream comprises at least 50 mg/l, in particular at least 100 mg/l, indeed even at least 200 mg/l, of trifluoroacetyl fluoride and/or trifluoroacetic acid.

According to one embodiment, boric acid is added to the acid solution used for the washing stage.

According to one embodiment, the gas stream is a stream resulting from a catalytic fluorination reaction of at least one chlorinated compound to give at least one fluorinated compound, said stream preferably being collected at the outlet of a distillation of a stream of products from the catalytic fluorination reaction.

According to one embodiment, the catalytic fluorination reaction is carried out in the presence of oxygen.

According to one embodiment:
- the chlorinated compound is a chlorocarbon, a hydrochlorocarbon, a chlorofluorocarbon, a hydrochlorofluorocarbon, a chloroolefin, a hydrochloroolefin, a chlorofluoroolefin or a hydrochlorofluoroolefin and the fluorinated compound is a fluorocarbon, a hydrofluorocarbon, a chlorofluorocarbon, a hydrochlorofluorocarbon, a fluoroolefin, a hydrofluoroolefin, a chlorofluoroolefin or a hydrochlorofluoroolefin;
- preferably, the chlorinated compound is chosen from 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene, 1-chloro-3,3,3-trifluoropropene and their mixtures; and
- preferably, the fluorinated compound is chosen from pentafluoroethane, 1-chloro-2,2-difluoroethane, 1,3,3,3-tetrafluoropropene, 2,3,3,3-tetrafluoropropene, 2-chloro-3,3,3-trifluoropropene, 1-chloro-3,3,3-trifluoropropene and their mixtures.

The invention also relates to a process for the preparation of a fluorinated compound, comprising:
- the provision of a chlorinated compound and of hydrofluoric acid;
- the catalytic reaction of the chlorinated compound with the hydrofluoric acid and the collection of a stream of crude products;
- the separation of the stream of crude products, preferably by distillation, making it possible to recover, on the one hand, a stream of fluorinated compound and, on the other hand, a gas stream mainly comprising hydrochloric acid and also minor amounts of hydrofluoric acid and of fluorinated-oxygenated compounds;
- the treatment of the gas stream comprising hydrochloric acid, hydrofluoric acid and fluorinated-oxygenated compounds as described above.

According to one embodiment, the catalytic reaction is carried out in the presence of oxygen.

According to one embodiment:
- the chlorinated compound is a chlorocarbon, a hydrochlorocarbon, a chlorofluorocarbon, a hydrochlorofluorocarbon, a chloroolefin, a hydrochloroolefin, a chlorofluoroolefin or a hydrochlorofluoroolefin and the fluorinated compound is a fluorocarbon, a hydrofluorocarbon, a chlorofluorocarbon, a hydrochlorofluorocarbon, a fluoroolefin, a hydrofluoroolefin, a chlorofluoroolefin or a hydrochlorofluoroolefin;
- preferably, the chlorinated compound is chosen from 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene, 1-chloro-3,3,3-trifluoropropene and their mixtures; and preferably, the fluorinated compound is chosen from pentafluoroethane, 1-chloro-2,2-difluoroethane, 1,3,3,3-tetrafluoropropene, 2,3,3,3-tetrafluoropropene, 2-chloro-3,3,3-trifluoropropene, 1-chloro-3,3,3-trifluoropropene and their mixtures.

The invention also relates to a plant for the treatment of a gas stream comprising hydrochloric acid, hydrofluoric acid and fluorinated-oxygenated compounds, comprising:

a pipe for introducing a gas stream comprising hydrochloric acid, hydrofluoric acid and fluorinated-oxygenated compounds, feeding a catalytic hydrolysis unit;

a washing unit, fed on the one hand by a pipe for collecting the hydrolyzed gas stream resulting from the catalytic hydrolysis unit and on the other hand by a pipe for introducing an acid solution;

a unit for adsorption of impurities comprising a bed of active charcoal, which unit is fed by a pipe for collecting the washed gas stream resulting from the washing unit;

a unit for adiabatic or isothermal absorption, fed on the one hand by a pipe for collecting the purified or isothermal stream resulting from the adsorption unit and on the other hand by a pipe for introducing an aqueous solution;

a pipe for collecting a hydrochloric acid solution at the outlet of the adiabatic or isothermal absorption unit.

According to one embodiment, the catalytic hydrolysis unit comprises a bed of active charcoal.

According to one embodiment, the pipe for introducing an acid solution does or does not result directly from the pipe for collecting a hydrochloric acid solution.

According to one embodiment, the plant additionally comprises:

an additional adsorption unit comprising a silica gel, which unit is fed by the pipe for collecting a hydrochloric acid solution; and a pipe for collecting a purified hydrochloric acid solution resulting from the additional adsorption unit.

According to one embodiment, the plan comprises a contribution of boric acid solution to the washing unit.

According to one embodiment, the pipe for introducing a gas stream comprising hydrochloric acid, hydrofluoric acid and fluorinated-oxygenated compounds results from a distillation unit, the distillation unit preferably being fed by a pipe for collecting crude products at the outlet of a catalytic reactor.

According to one embodiment, the catalytic reactor is fed by a pipe for introducing a chlorinated compound and a pipe for introducing hydrofluoric acid, and the pipe for collecting crude products transports a stream comprising a fluorinated compound, and preferably:

the chlorinated compound is a chlorocarbon, a hydrochlorocarbon, a chlorofluorocarbon, a hydrochlorofluorocarbon, a chloroolefin, a hydrochloroolefin, a chlorofluoroolefin or a hydrochlorofluoroolefin and the fluorinated compound is a fluorocarbon, a hydrofluorocarbon, a chlorofluorocarbon, a hydrochlorofluorocarbon, a fluoroolefin, a hydrofluoroolefin, a chlorofluoroolefin or a hydrochlorofluoroolefin;

more particularly, the chlorinated compound is chosen from 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene, 1-chloro-3,3,3-trifluoropropene and their mixtures; and more particularly, the fluorinated compound is chosen from pentafluoroethane, 1-chloro-2,2-difluoroethane, 1,3,3,3-tetrafluoropropene, 2,3,3,3-tetrafluoropropene, 2-chloro-3,3,3-trifluoropropene, 1-chloro-3,3,3-trifluoropropene and their mixtures.

According to one embodiment, the plant comprises a contribution of oxygen to the catalytic reactor.

The present invention makes it possible to overcome the disadvantages of the state of the art. It more particularly provides an improved process for the purification of the hydrochloric acid in a gas stream.

This is accomplished by virtue of the use of three successive stages of treatment of the gas stream, namely a stage of catalytic hydrolysis, a stage of washing and a stage of adsorption on active charcoal, this taking place before the stage of adiabatic or isothermal absorption which generates a concentrated hydrochloric acid solution.

The invention is based on the identification, by the present inventors, that the gaseous HCl recovered at the distillation column top may be contaminated by a small amount of free HF (entrained due to azotropes with light fluorinated compounds) but also by fluorinated-oxygenated compounds, such as carbonyl difluoride ($COF_2$), carbonyl chloride fluoride (COFCl) and trifluoroacetyl fluoride ($CF_3COF$).

These compounds are generated in particular when the gas stream to be treated results from a fluorination reaction carried out in the presence of oxygen.

These compounds are highly toxic and are hydrolyzable. They are thus capable of releasing HF, in particular during the stage of adiabatic or isothermal absorption in water, thus contaminating the HCl solution obtained with HF. In addition, the trifluoroacetyl fluoride generates trifluoroacetic acid (or TFA) during its hydrolysis, which compound is harmful.

The invention makes it possible to separate the HCl from the HF with which it is mixed but also to separate it from the abovementioned fluorinated-oxygenated compounds.

The invention is also based on the identification, by the present inventors, that the gaseous HCl recovered at the distillation column top may be contaminated by light organic compounds. The invention also makes it possible to satisfactorily remove these light organic compounds during the treatment.

BRIEF DESCRIPTION OF THE FIGURES

The FIGURE diagrammatically represents an embodiment of a plant according to the invention.

DESCRIPTION OF EMBODIMENTS OF THE INVENTION

The invention is now described in more detail and without implied limitation in the description which follows.

The invention applies in particular to the treatment of a gas stream resulting from a catalytic fluorination reaction of at least one chlorinated compound to give at least one fluorinated compound. The gas stream treated according to the invention can be directly the gas stream of products resulting from a reactor or more preferably a stream resulting from a distillation (carried out in a distillation column or in a series of several successive distillation columns) on conclusion of the catalytic fluorination. In this case, the gas stream to be treated according to the invention has been essentially separated beforehand from the fluorinated compound and/or from the unreacted chlorinated compound and/or from the byproducts of the reaction.

The gas stream to be treated according to the invention preferably predominantly comprises HCl, with minor amounts of contaminants, such as HF and the abovementioned fluorinated-oxygenated compounds (and in particular trifluoroacetyl fluoride).

The term "chlorinated compound" (with represents the main reactant of the catalytic fluorination reaction) is understood to mean an organic compound comprising one or more chlorine atoms and the term "fluorinated compound" (which represents the desired product from the catalytic fluorination reaction) is understood to mean an organic compound comprising one or more fluorine atoms.

It is understood that the chlorinated compound can comprise one or more fluorine atoms and that the fluorinated compound can comprise one or more chlorine atoms. Generally, the number of chlorine atoms of the fluorinated compound is less than a number of chlorine atoms of the chlorinated compound and the number of fluorine atoms of the fluorinated compound is greater than the number of fluorine atoms of the chlorinated compound.

The chlorinated compound can be an alkane or an alkene optionally having substituents chosen from F, Cl, I and Br (preferably from F and Cl) and comprising at least one Cl substituent.

The fluorinated compound can be an alkane or an alkene optionally having substituents chosen from F, Cl, I and Br (preferably from F and Cl) and comprising at least one F substituent.

The chlorinated compound can in particular be an alkane with one or more chlorine substituents (hydrochlorocarbon or chlorocarbon) or an alkane with one or more chlorine and fluorine substituents (hydrochlorofluorocarbon or chlorofluorocarbon) or an alkene with one or more chlorine substituents (chloroolefin or hydrochloroolefin) or an alkene with one or more chlorine and fluorine substituents (hydrochlorofluoroolefin or chlorofluoroolefin).

The fluorinated compound can in particular be an alkane with one or more fluorine substituents (fluorocarbon or hydrofluorocarbon) or an alkane with one or more chlorine and fluorine substituents (hydrochlorofluorocarbon or chlorofluorocarbon) or an alkene with one or more fluorine substituents (fluoroolefin or hydrofluoroolefin) or an alkene with one or more chlorine and fluorine substituents (hydrochlorofluoroolefin or chlorofluoroolefin).

The chlorinated compound and the fluorinated compound can be linear or branched, preferably linear.

According to one embodiment, the chlorinated compound and the fluorinated compound comprise just one carbon atom.

According to one embodiment, the chlorinated compound and the fluorinated compound comprise two carbon atoms.

According to one embodiment, the chlorinated compound and the fluorinated compound comprise three carbon atoms.

According to one embodiment, the chlorinated compound and the fluorinated compound comprise four carbon atoms.

According to one embodiment, the chlorinated compound and the fluorinated compound comprise five carbon atoms.

The invention finds in particular an application in the following fluorination reactions:
- fluorination of perchloroethylene (PER) to give pentafluoroethane (HFC-125);
- fluorination of 1,1,1,2,3-pentachloropropane (HCC-240db) to give 2-chloro-3,3,3-trifluoropropene (HCFO-1233xf);
- fluorination of 1,1,1,2,3-pentachloropropane (HCC-240db) to give 2,3,3,3-tetrafluoropropene (HFO-1234yf);
- fluorination of 1,1,1,3,3-pentachloropropane (HCC-240fa) to give 1,3,3,3-tetrafluoropropene (HFO-1234ze);
- fluorination of 1,1,1,3,3-pentachloropropane (HCC-240fa) to give 1-chloro-3,3,3-trifluoropropene (HCFO-1233zd);
- fluorination of 2-chloro-3,3,3-trifluoropropene (HCFO-1233xf) to give 2,3,3,3-tetrafluoropropene (HFO-1234yf);
- fluorination of 1,1,2,2,3-pentachloropropane (HCC-240aa) to give 2,3,3,3-tetrafluoropropene (HFO-1234yf);
- fluorination of 1,1,2,2,3-pentachloropropane (HCC-240aa) to give 2-chloro-3,3,3-trifluoropropene (HCFO-1233xf);
- fluorination of 2,3-dichloro-1,1,1-trifluoropropane (HCFC-243db) to give 2,3,3,3-tetrafluoropropene (HFO-1234yf);
- fluorination of 2,3-dichloro-1,1,1-trifluoropropane (HCFC-243db) to give 1-chloro-3,3,3-trifluoropropene (HCFO-1233zd);
- fluorination of 2,3-dichloro-1,1,1-trifluoropropane (HCFC-243db) to give 1,3,3,3-tetrafluoropropene (HFO-1234ze);
- fluorination of 2,3-dichloro-1,1,1-trifluoropropane (HCFC-243db) to give 2-chloro-3,3,3-trifluoropropene (HCFO-1233xf);
- fluorination of 1,1,2,3-tetrachloropropene (HCO-1230xa) to give 2,3,3,3-tetrafluoropropene (HFO-1234yf);
- fluorination of 1,1,2,3-tetrachloropropene (HCO-1230xa) to give 2-chloro-3,3,3-trifluoropropene (HCFO-1233xf);
- fluorination of 2,3,3,3-tetrachloropropene (HCO-1230xf) to give 2,3,3,3-tetrafluoropropene (HFO-1234yf);
- fluorination of 2,3,3,3-tetrachloropropene (HCO-1230xf) to give 2-chloro-3,3,3-trifluoropropene (HCFO-1233xf);
- fluorination of 1,1,3,3-tetrachloropropene (HCO-1230za) to give 1-chloro-3,3,3-trifluoropropene (HCFO-1233zd);
- fluorination of 1,1,3,3-tetrachloropropene (HCO-1230za) to give 1,3,3,3-tetrafluoropropene (HFO-1234ze);
- fluorination of 1,3,3,3-tetrachloropropene (HCO-1230zd) to give 1-chloro-3,3,3-trifluoropropene (HCFO-1233zd);
- fluorination of 1,3,3,3-tetrachloropropene (HCO-1230zd) to give 1,3,3,3-tetrafluoropropene (HFO-1234ze);
- fluorination of 1-chloro-3,3,3-trifluoropropene (HCFO-1233zd) to give 1,3,3,3-tetrafluoropropene (HFO-1234ze);
- fluorination of 1,1,2-trichloroethane to give 1-chloro,2,2-difluoroethane (HCFC-142);
- fluorination of 1,2-dichloroethylene to give 1-chloro-2,2-difluoroethane (HCFC-142).

The conversion of the chlorinated compound to give a fluorinated compound can be a direct conversion (with just one reaction stage or with just one combination of reaction conditions) or an indirect conversion (with two or more than two reaction stages or by using two or more than two combinations of reaction conditions).

The fluorination reaction can be carried out:
with an HF/chlorinated compound molar ratio of 3:1 to 150:1, preferably of 4:1 to 100:1 and more particularly preferably of 5:1 to 50:1;
with a contact time of 1 to 100 s, preferably 1 to 50 s and more particularly 2 to 40 s (catalytic volume divided by the total incoming stream, adjusted to the operating temperature and to the operating pressure);
at an absolute pressure ranging from 0.1 to 50 barg, preferably from 0.3 to 15 barg;
at a temperature (temperature of the catalyst bed) of 100 to 500° C., preferably of 200 to 450° C. and more particularly of 300 to 400° C.

In order to avoid rapid deactivation of the catalyst during the reaction, an oxidizing agent (for example oxygen or chlorine) can be added, for example in an oxidizing agent/organic compound molar ratio of 0.005 to 2, preferably of 0.01 to 1.5. It is possible, for example, to use a pure oxygen or pure chlorine stream or an oxygen/nitrogen or chlorine/nitrogen mixture.

Preferably, a stream comprising oxygen is used to carry out the fluorination (this use correspondingly resulting in the appearance of contaminants, such as trifluoroacetyl fluoride and fluorinated phosgene derivatives, in the stream of products).

The catalyst used can, for example, be based on a metal comprising a transition metal oxide or a derivative or a halide or an oxyhalide of such a metal. Mention may be made, for example, of $FeCl_3$, chromium oxyfluoride, chromium oxide (optionally subjected to fluorination treatments), chromium fluorides and their mixtures. Other possible catalysts are catalysts supported on carbon, antimony-based catalysts or aluminum-based catalysts (for example $AlF_3$ and $Al_2O_3$, aluminum oxyfluoride and aluminum fluoride).

Use may be made, in general, of a chromium oxyfluoride, an aluminum fluoride, an aluminum oxyfluoride or a supported or unsupported catalyst comprising a metal, such as Cr, Ni, Fe, Zn, Ti, V, Zr, Mo, Ge, Sn, Pb, Mg or Sb.

Reference may be made, in this regard, to the document WO 2007/079431 (on p. 7, l.1-5 and 28-32), to the document EP 939071 (section [0022]), to the document WO 2008/054781 (on p. 9, l.22-p. 10, l.34), and to the document WO 2008/040969 (claim 1), to which documents reference is expressly made.

Before its use, the catalyst is preferably subjected to activation with air, oxygen or chlorine and/or with HF.

Before its use, the catalyst is preferably subjected to activation with air or oxygen and HF at a temperature of 100 to 500° C., preferably of 250 to 500° C. and more particularly of 300 to 400° C. The activation time is preferably from 1 to 200 h and more particularly from 1 to 50 h.

This activation can be followed by a stage of final fluorination activation in the presence of an oxidizing agent, of HF and of organic compounds.

The HF/organic compound molar ratio is preferably from 2 to 40 and the oxidizing agent/organic compound molar ratio is preferably from 0.04 to 25. The temperature of the final activation is preferably from 300 to 400° C. and its duration is preferably from 6 to 100 h.

The catalyst is preferably based on chromium and it is more particularly a mixed catalyst comprising chromium.

According to one embodiment, use is made of a mixed catalyst comprising chromium and nickel. The Cr/Ni molar ratio (on the basis of the metal element) is generally from 0.5 to 5, for example from 0.7 to 2, for example of approximately 1. The catalyst can comprise from 0.5 to 20% by weight of chromium and from 0.5 to 20% by weight of nickel, preferably from 2 to 10% of each.

The metal can be present in the metallic form or in the derivative form, for example an oxide, halide or oxyhalide. These derivatives are preferably obtained by activation of the catalytic metal.

The support is preferably formed with aluminum, for example alumina, activated alumina or aluminum derivatives, such as aluminum halides and aluminum oxyhalides, for example described in the document U.S. Pat. No. 4,902,838 or obtained by the activation process described above.

The catalyst can comprise chromium and nickel in an activated or nonactivated form on a support which has or has not been subjected to activation.

Reference may be made to the document WO 2009/118628 (in particular on p. 4, l.30-p. 7 l.16), to which reference is expressly made here.

Another preferred embodiment is based on a mixed catalyst comprising chromium and at least one element chosen from Mg and Zn. The Mg or Zn/Cr atomic ratio is preferably from 0.01 to 5.

By now referring to FIG. 1, the plant according to the invention can comprise three successive treatment units, mainly a catalytic hydrolysis unit 2, a washing unit 4 and a unit for the adsorption of impurities 7, upstream of an adiabatic or isothermal absorption unit 9. An additional adsorption unit 13 is optionally provided downstream of the absorption unit 9.

The gas stream to be treated, which preferably constitutes a portion of a stream of catalytic fluorination reaction products (separated by distillation), is introduced by a pipe for introducing a gas stream 1 at the catalytic hydrolysis unit 2.

In this catalytic hydrolysis unit 2, the fluorinated-oxygenated compounds of the gas stream are hydrolyzed. The main hydrolysis reactions are as follows:

$$COF_2 + H_2O \rightarrow CO_2 + 2HF$$

$$COFCl + H_2O \rightarrow CO_2 + HCl + HF$$

$$CF_3COF + H_2O \rightarrow CF_3COOH + HF$$

The catalytic hydrolysis unit 2 is provided with a catalytic bed, which is preferably a bed of active charcoal. The temperature of the catalytic hydrolysis stage is preferably from 100 to 200° C., in particular from 120 to 170° C. and more particularly from 130 to 150° C. The pressure is preferably from 0.5 to 3 barg, in particular from 1 to 2 barg.

The residence time of the entities of interest in the unit is preferably from 1 s to 1 min, in particular from 2 s to 30 s, more particularly from 4 s to 15 s and very particularly from 5 s to 10 s.

The amount of water in the mixture subjected to the catalytic hydrolysis is adjusted so that the molar ratio of the water with respect to the sum of the fluorinated-oxygenated compounds is greater than 1, preferably greater than or equal to 2, or 3, or 4, or 5, or 6 or 6.5. A contribution of water may be provided, if necessary.

The degree of hydrolysis (molar proportion of fluorinated-oxygenated compounds hydrolyzed) is preferably greater than 90%, more particularly greater than 95%, than 98%, than 99%, than 99.5%, than 99.9%, than 99.95% or than 99.99%.

At the outlet of the catalytic hydrolysis unit 2, the gas stream is withdrawn in a pipe for collecting a hydrolyzed gas stream 3. This pipe feeds a washing unit 4. The washing unit 4 can be a plate column, such as a perforated plate column, or a bubble cap column, or a valve plate column or a column of Dualflow® type. It can also be a packed column. The washing of the gas stream is preferably carried out countercurrentwise: the gas stream is fed at the bottom and an acid solution is fed at the top, via a pipe for introducing an acid solution 6.

Use may in particular be made, as acid solution, of an HCl solution at a concentration by weight which can range, for example, from 5 to 60%, in particular from 10 to 50%, more preferably from 20 to 45% and in particular from 30 to 35%.

The washing by the acid solution is preferably carried out at a temperature of 5 to 50° C. and more particularly at 7 to 40° C.; and/or at a pressure of 0.1 to 4 barg, preferably of 0.3 to 2 barg and more preferably from 0.5 to 1.5 barg.

The efficiency of absorption of the HF and of the TFA in the acid solution depends on the number of theoretical plates installed, on the reflux ratio and on the temperature of the concentrated HCl solution. Generally, the HF is more easy to absorb than the TFA.

An addition of boric acid at the stage of washing with the acid solution makes it possible to complex the fluoride ions. For example, the addition of 2000 to 8000 ppm of $H_3BO_3$ makes it possible to improve the absorption effectiveness and to achieve TFA contents in the commercial HCl solution of less than 25 ppm. In other words, this boric acid addition solution makes it possible to install a column which exhibits a reduced number of theoretical stages and which operates with a lower reflux ratio, in order to obtain one and the same effectiveness of absorption of HF and of TFA in the concentrated HCl solution.

In the stage of washing with the acid solution, the great majority of the HF and of the TFA of the gas stream passes into solution and is thus removed via a pipe for collecting waste acid solution 15 at the column bottom. An additional hydrolysis of the fluorinated-oxygenated compounds possibly remaining in the gas stream may take place in the washing stage.

The washed gas stream resulting from the washing unit 4 is recovered via a pipe for collecting a washed gas stream 5. This pipe feeds a unit for the adsorption of impurities 7, which comprises a bed of active charcoal. The impurities adsorbed by the bed of active charcoal are first volatile organic compounds (VOCs).

This is because the gaseous HCl can be contaminated by light organic compounds entrained with it at the top of the distillation at very low contents (or at higher contents when the distillation is disturbed, for example). These light organic compounds can comprise trifluoromethane (F23), pentafluoroethane (F125), chloropentafluoroethane (F115), 1,1,1-trifluoroethane (F143a), fluoromethane (F41), trifluoropropyne, and the like. For example, F125 and F115 form an azeotrope with HCl.

The stage of adsorption on a bed of active charcoal can be carried out in pressure and temperature ranges which have already been indicated above in connection with the stage of washing with an acid solution.

At the outlet of the unit for adsorption of impurities 7, the purified gas stream is recovered in a pipe for collecting a purified stream 8 which is connected at the inlet of an adiabatic or isothermal absorption unit 9. The absorption unit 9 makes it possible to absorb the HCl of the gas stream in an aqueous solution, introduced by a pipe for introducing an aqueous solution 10. This aqueous solution can be simply demineralized water or can alternatively be an acid solution.

Generally, the absorption unit 9 comprises a column for bringing into contact countercurrentwise, the aqueous solution being provided at the top and the gas stream at the bottom.

As the reaction for absorption of the HCl in the water is exothermic, it is preferable to limit the pressure at which this operation is carried out. Generally, the pressure is less than 2 barg and preferably less than 1.5 barg. In this way, the absorption temperature does not exceed 130° C. and preferably 120° C. In order to withstand corrosion, the column can be made of graphite or else of steel coated with polytetrafluoroethylene (PTFE). The column internal parts can, for example, be either made of graphite or of polyvinylidene fluoride (PVDF).

A deacidified gas stream is gathered at the top, via a pipe for collecting a deacidified gas stream 11. This stream can either be discharged at the atmosphere via a neutralization safety column or sent to an incinerator.

An HCl solution is gathered at the bottom, via a pipe for collecting the hydrochloric acid solution 12. The concentration by weight of HCl in the solution can be from 5 to 50%, preferably from 15 to 40% and more particularly from 30 to 35%. A portion of this solution can be used as washing solution in the washing unit 4. In this case, the pipe for introducing an acid solution 6 can be connected to the pipe for collecting the hydrochloric acid solution 12. The proportion of HCl solution thus used for the requirements of the washing can represent from 2 to 15% by weight, preferably from 5 to 10%.

If the purity of the HCl solution collected is not sufficient and in particular if the HF content remains above the desired threshold, it is possible to proceed to another treatment stage, namely a stage of adsorption in an additional adsorption unit 13 fed by the pipe for collecting a hydrochloric acid solution 12. This additional adsorption unit 13 can comprise, for example, a silica gel.

The temperature of the HCl solution must be as low as possible and for example less than or equal to 35° C. as the adsorption on the silica gel is exothermic. Above this temperature, the adsorption effectiveness greatly decreases. The contact time is between a few minutes and a few hours (preferably between 10 and 60 min). The rates of passage are slow and between 1 and 20 m/h and preferably between 3 and 10 m/h. The operating pressure is a few bar (from 1 to 7 barg and preferably from 1 to 5 barg). The silica gel typically comprises a pore size of 50 Å, whereas conventional gels generally have pore sizes of 20 Å at most. The fluoride content of the HCl solution at the inlet is preferably less than or equal to 100 ppm in order to avoid any risk of damage to the silica gel. It is thus a finishing operation. After this additional stage of adsorption on silica gel, it is possible to achieve HF contents of less than 1 ppm in the HCl solution.

At the outlet of the additional adsorption unit 13, a purified HCl solution is recovered in a pipe for collecting a purified hydrochloric acid solution 14.

The HCl solution (or purified HCl solution) recovered on conclusion of the process of the invention can be put to use commercially.

Preferably, the maximum content of fluorides in this HCl solution (or purified HCl solution) recovered on conclusion of the process is 5 ppm, indeed even 1 ppm. The maximum content of fluorinated-oxygenated organic compounds (and in particular TFA) can be, for example, 25 ppm.

EXAMPLES

The installation comprises a hydrolysis oven fed using a pump and equipped with a gas positive-displacement meter specific for corrosive gases which makes possible the measurement of the incoming gas. The oven is also fed with water by a pump suitable for our flow rate range. The internal chamber of the oven is made of graphite (maximum temperature of 200° C.) and comprises a bed of active charcoal. The oven uses a system for heating by electromagnetic induction generated by an inductor made of copper. All the materials used for the construction of the oven are compatible with the corrosive gases handled.

The resulting gas stream is sent to the bottom of a plate column. The hydrochloric acid stream to be purified can also be sent directly to the plate column without passing through the hydrolysis oven. This device makes it possible to demonstrate the advantages of the hydrolysis oven. The column has a height of 1.20 meter and a diameter of five centimeters. It comprises twenty perforated plates (200 perforations per plate, each having a diameter of 1.75 mm). With a mean height of 1 cm of liquid per plate, a theoretical retention volume of 390 ml of liquid is achieved. The distance between the plates is equal to the diameter of the column. Each plate comprises a weir which makes possible the movement of the liquid toward the column bottom whereas the perforations allow the passage of the gas toward the column top. The preferred material for the column is PVDF. The column is fed with commercial 37% by weight liquid hydrochloric acid which will make it possible to wash and purify the anhydrous gas after it has or has not passed through the hydrolysis oven.

The device is installed as a branch circuit on an industrial plant, so as to treat a real gas. The flow rate of gas to be purified on this branch circuit is approximately 300 l/h. This gas results from a first distillation column which follows the catalytic fluorination reaction stage carried out in the gas phase in the presence of oxygen. In this distillation column, the predominant organic product is obtained at the column bottom while the anhydrous HCl (76 vol %) and the air (23 vol %) are separated at the column top. This HCl stream also comprises fluorinated organic impurities (1%), the most troublesome being $CF_3COF$ and $COF_2$. These impurities are subsequently reencountered in the hydrochloric acid solutions (in the fluoride and/or trifluoroacetic acid, also known as TFA, form) after their absorption and limit the economic value of the hydrochloric acid solutions obtained. The hydrolysis reactions under consideration are:

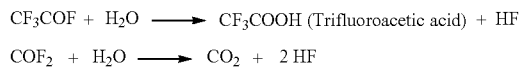

The impurities present in the hydrochloric acid gas before and after treatment are analyzed by ion chromatography of an aqueous solution into which the gas has sparged for a defined time and with a defined flow rate. Ion chromatography makes it possible to accurately evaluate the amounts of fluoride ions and trifluoroacetate $CF_3COO^-$ ions. The contents of impurities are expressed in ppm in a 33% hydrochloric acid solution in order to facilitate comparisons.

Example 1: Without Use of the Hydrolysis Oven

A flow rate of 265 l/h of gas to be purified predominantly comprising anhydrous hydrochloric acid is fed at the bottom of the perforated plate washing column. 332 g/h of 37% liquid hydrochloric acid solution are fed at the column top for the washing. After filling and equilibrating the plates, the test is maintained for 5 hours. The results obtained with regard to the content of impurities in the anhydrous gas are given in table 1.

Example 2: With Use of the Hydrolysis Oven

A flow rate of 295 l/h of gas to be purified, predominantly comprising anhydrous hydrochloric acid, is fed to the hydrolysis oven. The temperature of the oven is maintained at approximately 100° C. The oven is fed with water with a flow rate of 83.5 g/h. The resulting gas stream is subsequently fed to the bottom of the perforated plate washing column. 244 g/h of 37% liquid hydrochloric acid solution are fed at the column top for the washing. After filling and equilibrating the plates, the test is maintained for 4 h 30. The results obtained with regard to the content of impurities in the anhydrous gas are given in table 1.

TABLE 1 effect of the purification treatment without and with hydrolysis oven

| | ppm (weight) | | | |
| | Example 1 | | Example 2 | |
| | Inlet gas | Outlet gas | Inlet gas | Outlet gas |
|---|---|---|---|---|
| TFA/33% HCl | 2766 | 1624 | 2279 | 1 |
| F/33% HCl | 894 | 431 | 779 | 4 |

The limiting stage indeed appears to be the hydrolysis of the molecules, which takes place with difficulty in the washing column. On the other hand, once this hydrolysis is complete, the removal of the impurities by the strong acid wash process no longer appears to present problems. The combination of the two stages is thus necessary in order to obtain a good purity of the HCl.

The invention claimed is:

1. A process for treating a gas stream comprising hydrochloric acid, hydrofluoric acid and fluorinated-oxygenated compound, comprising successively subjecting the gas stream to the following stages:
   hydrolyzing in the presence of a catalyst;
   washing with acid solution;
   adsorbing impurities by active charcoal; and
   absorbing the hydrochloric acid in an aqueous solution by adiabatic or isothermal absorption to collect hydrochloric acid solution;
   wherein the fluorinated-oxygenated compound comprises carbonyl difluoride, carbonyl chloride fluoride, trifluoroacetyl fluoride and/or trifluoroacetic acid.

2. The process of claim 1, wherein the catalytic hydrolysis stage is carried out on a bed of active charcoal.

3. The process of claim 1, wherein the acid solution used during the washing stage is a hydrochloric acid solution.

4. The process of claim 1, further comprising subjecting the gas stream to a stage of bringing the hydrochloric acid solution into contact with a silica gel.

5. The process of claim 1, wherein boric acid is added to the acid solution used for the washing stage.

6. The process of claim 1, wherein the gas stream is a stream resulting from a catalytic fluorination reaction of at least one chlorinated compound to give at least one fluorinated compound.

7. The process of claim 6, wherein the catalytic fluorination reaction is carried out in the presence of oxygen.

8. The process of claim 6, wherein the chlorinated compound comprises a chlorocarbon, a hydrochlorocarbon, a chlorofluorocarbon, a hydrochlorofluorocarbon, a chloroolefin, a hydrochloroolefin, a chlorofluoroolefin or a hydrochlorofluoroolefin and wherein the fluorinated compound comprises a fluorocarbon, a hydrofluorocarbon, a chlorofluorocarbon, a hydrochlorofluorocarbon, a fluoroolefin, a hydrofluoroolefin, a chlorofluoroolefin or a hydrochlorofluoroolefin.

9. A process for preparing a fluorinated compound, comprising:
    providing a chlorinated compound and hydrofluoric acid;
    catalytically reacting the chlorinated compound with the hydrofluoric acid and collecting a stream of crude products;
    separating the stream of crude products to recover a stream comprising fluorinated compound and a gas stream comprising hydrochloric acid, hydrofluoric acid and fluorinated-oxygenated compound comprising carbonyl difluoride, carbonyl chloride fluoride, trifluoroacetyl fluoride and/or trifluoroacetic acid; and
    treating the gas stream comprising hydrochloric acid, hydrofluoric acid and fluorinated-oxygenated compound as in claim 1.

10. The process of claim 9, wherein the catalytic reaction is carried out in the presence of oxygen.

11. The process of claim 9, wherein the chlorinated compound comprises a chlorocarbon, a hydrochlorocarbon, a chlorofluorocarbon, a hydrochlorofluorocarbon, a chloroolefin, a hydrochloroolefin, a chlorofluoroolefin or a hydrochlorofluoroolefin and wherein the fluorinated compound comprises a fluorocarbon, a hydrofluorocarbon, a chlorofluorocarbon, a hydrochlorofluorocarbon, a fluoroolefin, a hydrofluoroolefin, a chlorofluoroolefin or a hydrochlorofluoroolefin.

* * * * *